United States Defensive Publication [19] (H) [11] T976,002

Vanderslice [43] Nov. 7, 1978

[54] TOOTHPASTE CONTAINING BENZYL HYDROXYETHYL CELLULOSE AS A BINDER

[76] Inventor: Charles W. Vanderslice, 3505 Golf View Dr., Newark, Del. 19702

[21] Appl. No.: 867,855

[22] Filed: Jan. 9, 1978

[51] Int. Cl.[2] ..... A61K 7/16; A61K 7/22

[52] U.S. Cl. ..... 424/49; 424/54

[57] ABSTRACT

Dentifrice compositions are disclosed which use as a binder and thickener specified modified hydroxyethyl cellulose ethers in place of the conventional carboxymethyl cellulose. Specifically, the ethers disclosed for such use are benzyl hydroxyethyl cellulose having a benzyl D.S. of about 0.09 to 0.15 and hydroxyethyl cellulose M.S. of about 2 to 2.5. Phenylhydroxyethyl or butyl groups in the same proportions can be present in lieu of the benzyl group. Other ingredients are conventional dentifrice ingredients. Such compositions are particularly useful in antiseptic toothpastes, making use of ionic antiseptic materials, since these specified cellulose ethers do not precipitate in ionic solutions as does carboxymethyl cellulose.

1 Claim, No Sheets Drawing,

9 Pages Specification

The file of this unexamined application may be inspected and copies thereof may be purchased (849 O.G. 1221, Apr. 9, 1968).